United States Patent
Trávníček

(10) Patent No.: US 9,029,079 B2
(45) Date of Patent: May 12, 2015

(54) METHOD OF BIOTECHNOLOGICAL PRODUCTION OF BOVINE HEMODERIVATIVE

(75) Inventor: Dušan Trávníček, Holice (CZ)

(73) Assignee: SVUS Pharma a.s., Hradec Králové (CZ)

( * ) Notice: Subject to any disclaimer, the term of this patent is extended or adjusted under 35 U.S.C. 154(b) by 929 days.

(21) Appl. No.: 13/138,484

(22) PCT Filed: Feb. 26, 2010

(86) PCT No.: PCT/CZ2010/000021
§ 371 (c)(1),
(2), (4) Date: Nov. 29, 2011

(87) PCT Pub. No.: WO2010/097060
PCT Pub. Date: Sep. 2, 2010

(65) Prior Publication Data
US 2012/0070463 A1  Mar. 22, 2012

(30) Foreign Application Priority Data
Feb. 26, 2009  (CZ) .................................... 2009-117

(51) Int. Cl.
*A01N 1/02* (2006.01)
*A61K 35/14* (2006.01)
*A23L 1/29* (2006.01)
*A61K 35/16* (2006.01)
*C12P 1/00* (2006.01)
*A23J 1/06* (2006.01)
*A23K 1/16* (2006.01)
*A23L 1/30* (2006.01)

(52) U.S. Cl.
CPC . *A61K 35/14* (2013.01); *A23L 1/29* (2013.01); *A61K 35/16* (2013.01); *C12P 1/00* (2013.01); *A23J 1/06* (2013.01); *A23K 1/1646* (2013.01); *A23L 1/30* (2013.01)

(58) Field of Classification Search
CPC ........... A61K 35/14; A61P 37/04; C12P 1/00; A23L 1/29
USPC ...................................... 435/2, 41; 424/278.1
See application file for complete search history.

(56) References Cited

U.S. PATENT DOCUMENTS

2005/0271674 A1 * 12/2005 Campbell et al. .......... 424/184.1

FOREIGN PATENT DOCUMENTS

| CZ | 228038 | 7/1994 |
| CZ | 279147 | 11/1994 |
| GB | 2101888 | 1/1983 |
| GB | 2101888 A * | 1/1983 |

OTHER PUBLICATIONS

Duarte, Renata et al. Bovine Blood Components: Fractionation, Composition, and Nutritive Value. Journal of Agricultural Food Chemistry. 1999. (47) pp. 231-236.*

* cited by examiner

*Primary Examiner* — Susan Hanley
*Assistant Examiner* — Nghi Nguyen
(74) *Attorney, Agent, or Firm* — Dykema Gossett PLLC

(57) ABSTRACT

A method of biotechnological production of a bovine hemoderivative comprising the steps of: freshly acquired animal blood matter is first fermented in several phases, the blood fermentation product obtained is dried, the dried fermentation product is separated, which is followed by ethanol extraction of the blood fermentation product in several phases, the blood fermentation product is then subjected to vacuum inspissation with subsequent stabilization after undesirable substances have been removed. The condensed extract is processed with etheric preparation during which the condensed blood fermentation product is subjected to ether precipitation, and the precipitate, thus obtained is separated from the solution of undesirable substances soluble in ether.

5 Claims, No Drawings

METHOD OF BIOTECHNOLOGICAL PRODUCTION OF BOVINE HEMODERIVATIVE

TECHNICAL FIELD

The invention concerns a biotechnological method of production of bovine hemoderivative. Freshly acquired animal-origin blood matter, i.e. fresh bovine blood is first fermented in several phases, usually in two phases, under increased heating air temperatures. The obtained blood fermentation product is dried, usually at temperatures from 30 to 100° C. The dried blood fermentation product is separated. This is followed by ethanol extraction of the blood fermentation product in several phases. The extract of the blood fermentations product is subjected to one vacuum inspissation, usually to a final concentration 20 times higher then the original concentration, with subsequent separation of undesirable substances. The extract condensed in this way is then subjected to one etheric preparation during which the condensed blood fermentation product is subjected to precipitation through diethyl ether, and the obtained precipitate is separated from the solution of undesirable phospholipids dissolved in the ether. Then the final product is standardized.

The invention concerns also the use of bovine hemoderivative.

BACKGROUND ART

The Czech A.O. no. 228 038 describes the method of production of tissue preparation from vegetable or animal tissue through extraction of these tissues with ethanol. The tissue is subjected to ethanol in multi-stage manner over the range of 3 to 100 days in the temperature range from 10 to 100 degrees Celsius (° C.), preferably from 70 to 85° C. The extract is then concentrated to 5 to 50% of the original volume, and is precipitated with ether or another solvent. The precipitate is washed with ether, dried, and the dried precipitate is dissolved.

The invention has the advantage of using the obtained preparation to treat and regenerate cells in living organisms. The extraction process is performed through extraction with the extraction solvent.

The extraction conducted in this way has the disadvantage of placing the extracted substance outside of the boiler, which results in greater energy loss, impacting negatively on the extraction process as it reduces its temperature. Another disadvantage is the presence of oxidizing atmosphere during this extraction, impacting negatively on the chemical stability of the extract. Still another disadvantage of this invention is the low selectivity of the one-step etheric preparation, i.e. that the undesirable substances in the precipitate are physically inaccessible for the action of ether. The precipitate is formed by a compact oily phase. There is a procedure described in the invention consisting in the precipitate containing the active substances being cleared of the undesirable phospholipid substances through another addition of ether, making it relatively difficult for an emulsion to form, i.e. for the micro particles of the precipitate to hold back phospholipids. It is thus clear that the purification of the precipitate from phospholipids is difficult, there is no quantitative removal of phospholipids from the precipitate, but the phospholipids are removed only partially. Moreover, this method requires, after the etheric preparation of the thickened ethanol extract of the blood fermentation product, a drying step for the ether to be removed. There is thus certain risk of explosion, and of ether escaping in the surrounding atmosphere so that possible contamination of the environment cannot be ruled out. The evaporation residue without ether becomes susceptible to microbial contamination, and is also exposed to oxidizing atmosphere so that there can be uncontrollable cleavage of the evaporation residue through the action of oxygen.

The Czech Patent no. 279 147 describes a method of biotechnological production of a product, stimulating the immunity of organisms, through extraction from animal matter. Freshly acquired animal blood matter is subjected to enzymatic cleavage in 2 phases. First, at temperatures in the range of 80-85° C. for 3 hours, and then, in the second phase, in the temperature range 70-75° C. for 48 hours. The obtained matter is then dried at 75-80° C. and at maximum humidity of 35% for 120-160 hours, and then disintegrated to granules sized 500 µm. After this, extraction flotation is carried out in blood matter uplift through circulation of the extracting agent formed by aliphatic alcohols with up to 4 atoms, with maximum water content of up to 5%, under simultaneous heating to 50-55° C. Permanent contact of the extracted medium with the extracting agent is ensured through keeping e.g. the disintegrated fermentation product in the uplift. Using precipitation, lipidic parts are removed from the extract obtained in this way. Standardization of the final product is accomplished through modification of active substances in aqueous solution only, and the microbiological stability of the final product is not solved.

The advantage of this invention consists in its low energy intensity in the field of ethanol extraction as there is significant separation of the condensation heat of the extraction solvent from the process. The controlled fermentation is obviously associated with higher production of active substances compared to the previous invention.

This invention has the disadvantage that the extraction process is performed with maceration method during which there is no precipitation of the extracted blood salts in the heating register but pass through the entire technological process up to the final product. Undesirable blood salts are not eliminated because of the low extract concentration used which results from using a high surplus of the extraction solvent—ethanol with respect to the extracted substance—fermented blood. The patent solves this negative aspect through the application of a cooling process that is, however, not sufficiently effective regarding the removal of undesirable blood salts. This is a short process at low temperature so that one can anticipate that the process of separation of undesirable substances occurs with low efficiency. Moreover, after etheric preparation, the precipitate is dissolved in distilled water so that there are a total of three solvents present, ethanol in traces, diethyl ether in significant amount, and distilled water that as the dominant solvent. After subsequent vacuum evaporation of ether, possibly also of ethanol, a predominantly aqueous solution forms that is susceptible to microbial development. In this case as well, the one-step etheric preparation is insufficient in the sense of obtaining pure final product. Another disadvantage is to be seen in the fact that the fermentation in the second phase takes relatively long time, about 48 hours at temperatures of 70-75° C., which impacts significantly on the economics of the fermentation process. The separation of blood fermentation product to particles of up to 0.5 mm in size is necessary for the subsequent extraction process, carried out through maceration in the uplift. The final product exhibits visibly crystalline structure, as a result of the manufacturing procedure according to this invention, as a result of the undesirably high content of blood salts.

A disadvantage shared by both aforesaid inventions that are both based on bovine ferment, is the presence of undesirable substances that dilute the concentration of the active substance, and some of them can possibly be subject to oxidation or to rancidity of the final product.

SUBJECT MATTER OF THE INVENTION

The above-mentioned disadvantages are removed or substantially reduced when a method of biotechnological production of the bovine hemoderivative is used according to the present invention. Freshly acquired animal blood matter is first fermented in several phases, the blood fermentation product obtained is dried, the dried fermentation product is separated, which is followed by ethanol extraction of the blood fermentation product in several phases, the blood fermentation product is then subjected to vacuum inspissation with subsequent stabilization after undesirable substances have been removed. The condensed extract is processed with etheric preparation during which the condensed blood fermentation product is subjected to ether precipitation, and the precipitate thus obtained is separated from the solution of undesirable substances soluble in ether.

The subject matter of this invention concerns the fact that animal blood matter obtained immediately through fermentation, preferably bovine blood, is put into small containers so that the blood matter level reaches the height of 2.5-3 cm, and is gradually heated till it reaches the temperatures of 55-65° C. in its mass, preferably 60° C., after which the second fermentation phase occurs during which the temperature of the surrounding heating air drops, from around 80° C. in the first phase to 65-75° C., preferably +70° C. When this temperature has been reached the second fermentation phase takes place, during which a constant temperature difference of 5° C. is maintained between the heating air and blood matter temperatures for 5-20 hours, preferably 12 hours, during which autoenzymatic cleavage of the blood matter takes place. During this second fermentation phase, the entire blood matter assumes gummy (gluey) consistency, which ends the second fermentation phase.

The defined blood matter level height is optimum for the enzymatic processes to proceed effectively. This height of the level has been established in experiments. If the height of the level was higher it would impact more positively on the enzymatic processes, but the heat transfer during the first fermentation phase would not be sufficient to obtain the pasteurization temperature rapidly. Lower levels would result in shorter durations of the fermentation process, and utilization rate of the material introduced would therefore be lower.

The fermentation according to this invention is achieved over shorter period of time and is therefore more advantageous economically compared with existing technologies. The definition of optimum temperature value in the matter provides the solution of the rapid onset of pasteurization temperature, i.e. the microbial contamination is ruled out and autoenzymatic cleavage of the blood mater is started in the second fermentation phase. If the temperature were higher there would ensue out-of-proportion shortening of the fermentation time in the second phase. If the temperature was lower the efficacy of the second phase fermentation would be reduced, and undesirable microbial development would occur with higher probability. The defined time intervals for the two fermentation phases have been obtained through long-term operative tests.

The blood fermentation product obtained is dried through controlled ventilation according to a drying curve at 60-80° C. for 120-160 hours, preferably at 70° C. for 140 hours till the final humidity content of up to 10%, preferably 2-3% humidity. The controlled ventilation is optimized after the termination of the second phase of fermentation with regard to the operation economics, maintaining the quality of the fermentation product obtained. The defined drying temperatures and times are the result of long-term experimental testing. The defined humidity is optimum in the light of minimum introduction of water into the technology process for the subsequent extraction.

The dried fermentation product is subsequently separated to particles sized 1-10 mm, preferably 2-4 mm. The claimed particle size is optimum for the subsequent extraction process with ideal rheological properties, i.e. to attain small resistance of the particle layer relative to the extraction solvent flow rate in the process of subsequent extraction, but to avoid extension of the extraction time that would be associated with particle sizes exceeding 4 mm.

The separated blood fermentation product is subjected to continual extraction in several phases, preferably 4 phases, with permanently pure ethanol in an extractor of Soxhlet type, with a total extraction time of 200-400 hours, preferably 240 hours, at 70-78° C., the extracts of blood fermentation products being joined during repeated extraction. The extraction of the blood fermentation product in several phases according to the present invention is advantageous for obtaining permanently pure extracting agent, the action of which on the blood fermentation product at a temperature close to boiling point makes it possible to reduce the amount of ethanol used in the process, and to employ the process of concentration of the obtained extract in the boiler area, with continual separation of the precipitated undesirable blood salts. The extractor of Soxhlet type with heating of the extracted fermentation product is ideal for this method. Each individual extraction results in obtaining extract that is centralized in a single receiving vessel. The number of 4 extractions is advantageous and has undergone tests proving it to be sufficient for obtaining the maximum possible amount of extracted substances. The defined temperature range is optimum for the speed of the extractions, and the time used is necessary in view of the broad range of extracted desirable substances.

The joined blood fermentation product extracts are subjected to stabilization of the product obtained through separation of the blood salts using ambient temperature for 24-120 hours, preferably 72 hours, with the total stabilization time counted from the start of the process of obtaining the last blood fermentation product extract. The purpose of the stabilization is to remove undesirable blood salts that are eliminated over the course of time during individual technological operations.

After subsequent vacuum inspissation, the stabilized condensed blood fermentation product extract is subjected to etheric preparation over several phases to obtain the bovine hemoderivative precipitate, each of the precipitates arising in the process being dissolved in ethanol in amount till quantitative dissolution of the bovine hemoderivative precipitate and the formation of true bovine hemoderivative solution for the subsequent etheric preparation, and the solution over the decanted precipitate containing undesirable phospholipids soluble in diethyl ether is separated. The lipids enclosed in the oily bovine hemoderivative precipitate are made accessible to further action of ether through their dissolution in ethanol.

Following repeated preparation, the bovine hemoderivative precipitate obtained is stabilized to achieve separation of the residual undesirable ether from this precipitate.

The stabilized bovine hemoderivative precipitate is first dissolved in ethanol till true solution forms that is then subjected to vacuum inspissation at 25-40° C., preferably at 28° C., till distillate without ether is obtained. The dissolution in ethanol is an advantage compared to dissolution in water as it results in a microbially stable solution that persists to the final stage, i.e. the technological step of standardization. It evaporates easily the ether that is already undesirable from the ethanol solution at the given temperatures.

The obtained evaporation residue of the bovine hemoderative is dissolved in distilled water to a concentration of 50-500 g in 1 liter solution. The obtained aqueous ethanol solution is centrifuged using a cooled centrifuge to remove undissolved substances, and the supernatant thus formed is standardized after the separation of the undissolved substances in the sediment to a concentration of bovine hemoderivative of 50-500 g in 1 liter solution and to the required ethanol concentration in the range of 16-19% by weight. It is only in this technological step that distilled water is used as solvent for the first time, the reason being that the final ethanol concentration must remain at the declared level of 16-19% by weight that ensures microbial stability of the solution. Possibly arising insoluble substances are removed from this aqueous-ethanol environment simultaneously, preferably with centrifugation in cooled centrifuge. The cooling of the centrifuge is used because of the danger that the bovine hemoderivative could be heated during the centrifugation which could result in its thermal degradation.

The main advantage of the present invention is that a high-quality, microbially and chemically stable product is obtained with high bovine hemoderivative content, and with minimum or no content of undesirable phospholipids and blood salts, and the use of a procedure that is, starting with the ethanol extraction phase, always protected from microbial contamination and oxidative action of air. Any process in which only the aqueous solution would be present is ruled out, that is the presence of water as solvent that is highly susceptible to the development of microorganisms when biological substances are present. The fact that fresh solvent is permanently supplied in the process of extraction results in obtaining an extract with higher concentration, which has a clearly positive effect on the subsequent gradual separation of the undesirable organic salts. Repeated etheric preparation based on periodically arising bovine derivative precipitate that is then dissolved to true solution makes it possible to achieve almost quantitative separation of lipidic substances. Related to the existing technologies used to obtain the bovine hemoderivative, the method according to the present invention is faster and more ecological.

The ethanol extraction of the blood fermentation product and/or vacuum inspissation of the blood fermentation product extract, and/or vacuum inspissation of the ethanol-ether bovine hemoderivative can be advantageously carried out in a protective, e.g. nitrogen atmosphere. The entry of nitrogen into the extraction apparatus or vacuum circulation evaporator, in the course of the extraction process or vacuum circulation inspissation, creates a flow of bubbles in ethanol or the extract that stirs up the fluid and prevent the occurrence of latent boil of the extract or pure ethanol. The atmosphere over the surface (level) of the extract or the solution of bovine hemoderivative during vacuum inspissation serves the protective function of an inert gas against the oxidizing action of oxygen at the same time.

According to the present invention, the use of the bovine hemoderivative in aqueous-ethanol solution containing 50-500 g bovine hemoderivative in 1 liter of aqueous-ethanol solution, containing 16-19% by weight of ethanol, is suitable for the preparation of a dietetic used to enhance the immunity of organism in human and veterinary use. The use in humans does not include only dietetics or medicinal products, but also cosmetics.

EXAMPLES OF CARRYING OUT THE INVENTION

Example 1

The method of biotechnological production of bovine hemoderivative is presented in the following overview providing a summary of the whole progress of individual technological operations in time sequence (Flow-Sheet):

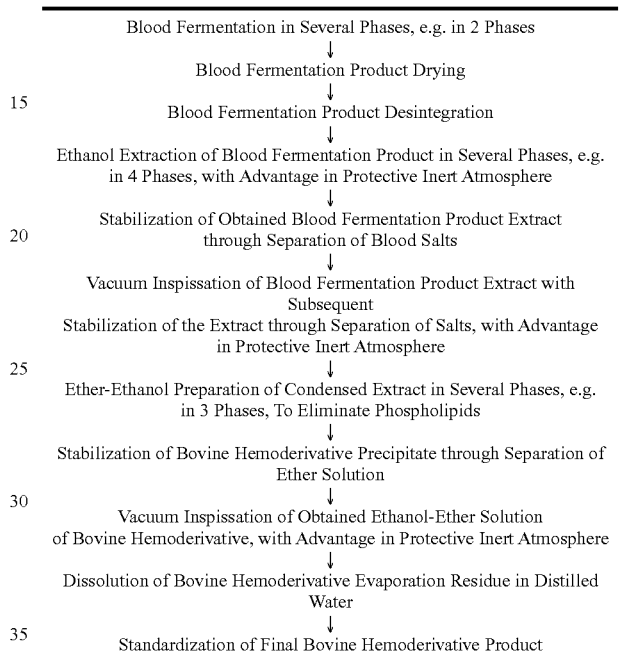

Example 2

A specific example embodiment is further described in individual technological operations, following one after another.

Fermentation of Bovine Blood in Two Phases

Raw bovine blood is disintegrated in the transport container using a high-pitched agitator to particles with maximum size of 30 mm. The separated blood is decanted into small rust free containers so that the level height of the mass is 2.5-3 cm.

This is followed by fermentation in two phases, i.e. autoenzymatic cleavage under the action of warmth, time and the enzymes contained in the raw blood.

The fermentation in the first phase proceeds as follows. The containers with blood mass are inserted into a drier apparatus, whereby the starting temperature of the blood mass should be at least 30° C. A temperature recorder is submerged into one selected container, the drier apparatus is closed, and heating temperature of the inner space of the apparatus is set to a value of about 75-85° C., preferably 80° C., for 2-2.5 hours. The drier apparatus is switched on in internal air circulation mode.

The second fermentation phase starts when the temperature in the blood mass reaches the temperature range 55-65° C., preferably 60° C. From this time on the heating air temperature is regulated so that the difference between the temperature of the blood mass and that of the heating air remain constant for the entire fermentation time, with a difference of 5° C. During this second fermentation phase, the blood mass assumes a gummy (gluey) consistency which terminates the second fermentation phase.

Blood Fermentation Product Drying

The fermented blood mass obtained in this way is cut to parts when warm, e.g. 10×10 cm. Then the blood fermentation product is subjected to drying in a drier apparatus at 60-80° C., preferably at 70° C. Drying of the small cut parts of the blood fermentation product is carried out in a drier apparatus, in controlled ventilation mode.

The rate of ventilation of the drier apparatus internal atmosphere is controlled by a drying curve that is terminated after 120-160 hours, preferably after 132-156 hours, to a obtain a final humidity content of up to 1-10% in the blood fermentation product, preferably 2-3% humidity.

Blood Fermentation Product Separation

The dried blood fermentation product is then disintegrated to optimum particle size, 1-10 mm, preferably 2-4 mm that is most suitable for subsequent technological operations.

Ethanol Extraction of Blood Fermentation Product in Four Phases

Continual extraction of the dried blood fermentation product obtained in this way is carried out using permanently pure ethanol, in a Soxhlet-type extractor, at 60-78° C., preferably closer to the upper limit, 78° C., in 96% ethanol. Higher temperatures facilitate the extraction of dried blood fermentation product.

Fermented blood is placed into an extraction cage, with perforated bottom and overflow placed above the level of the extracted substance. To the blood fermentation product 96% ethanol is added in an amount of at least ⅓ of its weight to allow the required reaction to proceed. The more ethanol is added, the faster and more effective is the extraction, though excessive ethanol surplus impacts negatively on the extraction economics and there may result the situation of great ethanol surplus that has then to be removed with difficulty. The dried blood fermentation product is thus covered with a layer of 96% ethanol in a way where about 35% of the total ethanol is located in the boiler area, the rest in the extraction cage.

The first extraction proceeds as follows: after the first 3-40 extraction hours, preferably after 24 hours, the first obtained extract is let out from the boiler into an extract tank located outside of the extractor. The extractor boiler area is then cleaned with warm water to remove the eliminated salts.

96% ethanol is again poured to the extractor boiler. The second and the following two extractions of the blood fermentation product not extracted so far carry on. The extraction process is interrupted after 20-60 hours, preferably during the 48th hour after the second extraction phase has been terminated, and the second blood fermentation product extract is obtained, and after another 50-90 hours, preferably in the 72nd hour for the third extraction phase has been terminated, and the third blood fermentation product extract is obtained. During the second and third extractions the same operations are carried out as in the first extraction phase terminated after 24 hours of extractor operation. This means that the amount of ethanol added in the third extraction phase is the same as in the second phase.

The obtained second and third blood fermentation product extracts are let out into the extract tank after each extraction is terminated.

The last, fourth extraction is terminated after 150-400 hours, preferably in the 240th hour. After this last, fourth extraction the last, fourth extract is let out into the extract tank. This means that the four extraction result in obtaining four joined blood fermentation product extracts in the extract tank.

These selected extraction times are chosen to be optimum in the light of extract acquirement. Short times of individual extraction phases would pose the risk of lower blood fermentation product extract yield. Longer times of individual extraction phases would result in unnecessary thermal burden to the extraction fractions already extracted that must be kept in the extractor boiler at boiling point to obtain pure ethanol steam for the subsequent extraction.

Ideal weight ratio of the inserted fermented blood to the added 96% ethanol is 1/3-20/1 for all four extraction phases.

The ethanol extraction carried out in this way results in obtaining a relatively concentrated joined blood fermentation product extract that is, compared with e.g. the procedure according to CS 228 038 and 279 147, is 7 to 8 times more concentrated, the amounts of inserted blood fermentation product being the same.

This ethanol extraction can be carried out in protective inert, e.g. nitrogen atmosphere, which rules out the occurrence of latent ethanol boil, or of the produced extract, and makes it possible at the same time that the positive effects of inert atmosphere, namely on the chemical stability of the extracted substances in particular manifest.

Stabilization of Blood Fermentation Product Extract Through Blood Salt Separation The joined blood fermentation product extract obtained in this way is stabilized in the extract tank for 24 to 120 hours, preferably for 72 hours, at ambient temperature, to separate the undesirable blood salts, e.g. ferrocyanides and other. The effectiveness of the stabilization increases with its duration. The stabilization may even proceed for one year, but this is disadvantageous economically. Undesirable blood salts are subsequently filtered off, or the clarified blood fermentation product extract solution is pumped off to another tank.

Vacuum Inspissation of Flood Fermentation Product Extract

The filtered blood fermentation product extract is gradually pumped off from the extract tank to a vacuum circulation evaporator. Here, the superfluous ethanol is evaporated from the extract at 40-70° C., preferably at 50-60° C.

The inspissation is performed in the ratio 1:5-1:40, preferably 1:20 ratio, meaning the ratio of the final condensed concentrated extract to the inserted extract, i.e. the concentration corresponds for example to an advantageous 20 fold concentration of the blood fermentation product extract. Immediately after the evaporation is terminated the extract condensed in this way is let off, while still warm, from the boiling area of the evaporator to the distillation receiver where it undergoes stabilization.

Vacuum inspissation of the blood fermentation product extract can be performed in protective inert, e.g. nitrogen, atmosphere. This prevents the occurrence of latent boiling of the extract. The inert atmosphere supports especially the chemical stability of the extracted substances.

Stabilization of Condensed Blood Fermentation Product Extract Through Separation of Salts Stabilization of the obtained condensed blood fermentation product extract is performed for 24-120 hours, preferably 72 hours, at ambient temperature. This stabilization is also performed to remove the remaining the undesirable fractions of blood salts that subside to the bottom or precipitate on the walls of the stabilization vessel. During the stabilization, the remaining undesirable blood salt fractions crystallize on the bottom or walls of the stabilization vessel. The undesirable blood salts are removed with filtration, or the clarified blood fermentation product extract solution is pumped off.

Ether-Ethanol Preparation of Condensed Blood Fermentation Product Extract in Three Phases This condensed and stabilized blood fermentation product extract is then filtered off from the precipitated undesirable blood salts. The obtained ethanol filtrate of the blood fermentation product extract is poured into a vessel with a propeller stirrer for phospholipid separation. The preparation is carried out through multiple precipitation of the blood fermentation product extract with 100% diethyl ether, resulting in the formation of a precipitate containing the bovine hemoderivative and a solution overlying the precipitate that contains undesirable phospholipids soluble in diethyl ether that are separated from the precipitate in each preparation phase. The bovine hemoderivative precipitate is dissolved in ethanol.

In more detail: The first phase of blood the preparation of the fermentation product extract is carried out through the action of diethyl ether such that the diethyl ether is added in parts under permanent stirring in a volume-amount ratio 1:1-20:1 to the condensed blood fermentation product extract, preferably in the ratio to the double amount of the latter. This first phase of ether preparation of the blood fermentation product extract results in obtaining eliminated bovine hemoderivative precipitate that is allowed to sediment freely, and the ethanol-ether solution overlying the precipitate is separated.

The second phase of preparation of the bovine hemoderivative precipitate is carried out through the action of ethanol such that the bovine hemoderivative precipitate from the first phase is dissolved in 96% ethanol, using an amount of ethanol resulting in quantitative dissolution of the bovine hemoderivative precipitate to a true solution. This solution is then again precipitated with diethyl ether till a precipitate of the bovine hemoderivative forms. The solution formed in this way, overlying the precipitate, is separated.

In the third preparation phase, the precipitate from the second phase is used, and is dissolved in 96% ethanol, again used in amount till a solution forms, and this solution is again precipitated with diethyl ether. The solution overlying the precipitate is removed.

Stabilization of Bovine Hemoderivative Precipitate Through Separation of Ether Solution The precipitate formed in this way is allowed to stabilize for 10-40 hours, preferably 24 hours, at 10-40° C., preferably at 20-30° C., to obtain maximum possible separation of the bovine hemoderivative precipitate from the diethyl ether containing the last fractions of undesirable phospholipids. It is possible that the preceding operation has occurred almost quantitatively, and no solution forms over the bovine hemoderivative precipitate. Most of the time, however, there is some presence of diethyl ether solution. A possibly arising solution, separated from the precipitated, is pumped off, and the bovine hemoderivative precipitate obtained is then processed using the following method. The ideal weight ratio of the fermented blood to the 96% ethanol added is 1/3-20/1 for all four extraction phases, depending on qualitative variability of the raw blood input.

Vacuum Inspissation of Ethanol-Ether Solution of Bovine Hemoderivative

The precipitate obtained in the previous operation is dissolved in 96% ethanol, using amounts resulting in solution. This solution is inserted in a rotating vacuum evaporator, and air from the evaporator is displaced using a combination of negative pressure and supply of protective atmosphere, e.g. nitrogen. The mixture of residual diethyl ether and part of the ethanol is evaporated from the solution in the rotating vacuum evaporator, at 25-40° C., preferably 28° C. The aim of this evaporation is to maximally evaporate the diethyl ether, the amount of evaporated ethanol being kept at minimum. Evaporation is terminated when there zero content of diethyl ether in the vapor over the evaporated solution has been attained. This operation ensures microbial stability through the action of highly concentrated of ethanol in the solution. The evaporation in vacuum carried out simultaneously protects the active substance, the bovine hemoderivative, from the oxidative action of air.

Vacuum evaporation accomplished in this way is advantageous not only for the removal of ether, but protects the bovine hemoderivative from the thermal burden and the oxidative action of air at the same time. The vacuum atmosphere in the vacuum evaporator lowers the boiling point of the evaporated bovine hemoderivative solution. The use of inert atmosphere, e.g. nitrogen atmosphere, in the evaporator prevents the oxidative action of oxygen on the bovine hemoderivative.

Dissolution of Bovine Hemoderivative Evaporation Residue in Distilled Water

The obtained evaporation residue with partial ethanol content is analyzed to determine its contents of ethanol and dry matter, or the content of dry matter in the bovine hemoderivative is determined. Depending on this dry matter content the evaporation residue is diluted with sterile distilled water to aqueous-ethanol solution. The amount of water is chosen according to the required bovine hemoderivative concentration, i.e. the final product, usually in the range of 50-500 g bovine hemoderivative in 1 liter solution.

Standardization of Final Bovine Hemoderivative Product

The solution obtained in this way is then cooled to 2-15° C., preferably to 4-8° C., and centrifuged in a cooled centrifuge at 3-20 G, preferably 15 G, for 30-90 minutes, preferably 60 min. This removes all undesirable undissolved substances that form a sediment that is removed. The supernatant, the solution above the sediment that contains the bovine hemoderivative, is modified with ethanol solution, both to obtain the required concentration of bovine hemoderivative in 1 liter solution and so that the ethanol concentration is in the interval 16-19% by weight, obtaining the final product. The given ethanol content ensures microbial stability of the final product.

The final bovine hemoderivative product is visually characterized by amorphous structure, which is the result of the production method according to the present invention, during which the content of undesirable admixtures is removed or substantially restricted to minimum.

Auxiliary Operations

The ethanol-ether solution containing lipids is rectified in order to restore the solvents.

The extracted fermented blood is subjected to vacuum drying, also in order to renew the solvent, ethanol.

Use of Bovine Hemoderivative

The method of production of bovine hemoderivative serves the purpose to prepare of a natural dietetic to be used as dietary supplement or medicinal product, to enhance the immunity of organisms, for its use in humans and for veterinary purposes. The use in humans is defined as the field of nutrition and the pharmaceutical field, as well as the field of cosmetics. Bovine hemoderivative can be used in various forms, as a solution, e.g. for oral use, as injection, or in the form of tablets, capsules, or in the form of creams and foams.

The invention claimed is:
1. A method of biotechnological production of bovine hemoderivative, the method comprising:
 a) acquiring fresh bovine blood and fermenting said acquired blood in two phases comprising the steps of:

in a first fermentation phase, putting said acquired blood into containers wherein the blood mass level height is 2.5-3 cm in the containers and gradually heating the surrounding air temperature to 80° C. and the temperature of the acquired blood reaches a temperature of 55-65° C.;

decreasing the surrounding air temperature to 65-75° C. to begin a second fermentation phase and when the decreased surrounding air temperature is reached, the second fermentation phase proceeds during which a constant temperature difference of 5° C. is maintained between the surrounding air and the temperature of said blood, during which phase autoenzymatic cleavage of blood takes place until the entire blood passes into a gummy consistency to yield a blood fermentation product;

b) drying said obtained blood fermentation product through controlled ventilation according to a drying curve at 60-80° C. for 120-160 hours to a final humidity content of up to 10% to a dried blood fermentation product;

c) disintegrating said dried blood fermentation product to particles sizes of 1-10 mm;

d) extracting said resultant disintegrated dried blood fermentation product by continual extraction in four phases through the action of pure ethanol in an extractor of Soxhlet type, using a total extraction time of 150-400 hours at 70-78° C., and joining the resultant extracts of dried blood fermentation products, wherein said obtained joined extracts are subjected to stabilization through separation of undesirable blood salts, at ambient temperature for 24-120 hours to obtain a stabilized blood fermentation product;

e) subsequently, the stabilized blood fermentation product is subjected to one vacuum inspissation to a resulting concentration that is approximately 20 times higher than the original concentration, f) after subsequent vacuum inspissation, the resultant stabilized condensed blood fermentation product extract is subjected to ether preparation in several phases to obtain a precipitate of a bovine hemoderivative, then dissolving said precipitate in ethanol to obtain a solution of the bovine hemoderivative; subjecting the solution to a second ether preparation to obtain a mixture of a second precipitate having a solution overlying the second precipitate which contains undesirable phospholipids soluble in ether;

g) dissolving the mixture in ethanol until a true solution forms, and subjecting the true solution to vacuum inspissation at 25-40° C. until a plain ether distillate and an evaporation residue are obtained; and h) whereupon the evaporation residue containing ethanol is standardized to obtain a concentration of the bovine hemoderivative in water.

2. The method according to claim 1 h), wherein the standardization is carried out by dissolving the evaporation residue of the bovine hemoderivative in distilled water to a required concentration of 50-500 g in 1 liter solution and the obtained aqueous-ethanol solution is centrifuged a in cooled centrifuge to remove undissolved substances, and the formed supernatant, after separation of the sediment of undissolved substances, is standardized to the concentration of bovine hemoderivative of 50-500 g in 1 liter solution and to an ethanol concentration in the range of 16-19% by weight.

3. The method according to claim 1, wherein the ethanol extraction of the blood fermentation product and/or vacuum inspissation of the blood fermentation product extract, and/or vacuum inspissation of the ethanol-ether bovine hemoderivative is carried out in protective inert nitrogen atmosphere.

4. The method according to claim 1 a), wherein the temperature of the acquired blood reaches a temperature of 60° C. in the first fermentation phase.

5. The method according to claim 1 a), wherein the temperature of the surrounding air temperature is decreased to 70° C. to begin the second fermentation phase.

* * * * *